(12) United States Patent
Shifrin et al.

(10) Patent No.: US 7,694,866 B2
(45) Date of Patent: Apr. 13, 2010

(54) METHOD AND APPARATUS FOR LAPAROSCOPIC AORTIC REPAIR BY INTRAVASCULAR DEVICES

(75) Inventors: Edward G. Shifrin, 64 Ha-Shahar Street, Raanana 43565 (IL); Mark A. Umansky, Haifa (IL); Mordehy D. Shvartsman, Haifa (IL); Gennady S. Nickelshpur, Haifa (IL); Wesley S. Moore, Los Angeles, CA (US)

(73) Assignee: Edward G. Shifrin (IL)

( * ) Notice: Subject to any disclaimer, the term of this patent is extended or adjusted under 35 U.S.C. 154(b) by 335 days.

(21) Appl. No.: 10/593,758

(22) PCT Filed: Feb. 23, 2005

(86) PCT No.: PCT/IL2005/000218

§ 371 (c)(1),
(2), (4) Date: Jun. 18, 2007

(87) PCT Pub. No.: WO2005/089059

PCT Pub. Date: Sep. 29, 2005

(65) Prior Publication Data

US 2008/0021500 A1    Jan. 24, 2008

(30) Foreign Application Priority Data

Mar. 24, 2004    (IL) .................................... 161067

(51) Int. Cl.
*A61B 17/115* (2006.01)
(52) U.S. Cl. ...................................... 227/179.1; 227/19
(58) Field of Classification Search .............. 227/179.1, 227/19; 606/142, 143; 623/1.36, 1.11
See application file for complete search history.

(56) References Cited

U.S. PATENT DOCUMENTS

| 5,104,399 | A | 4/1992 | Lazarus ..................... 623/1.14 |
| 5,219,355 | A | 6/1993 | Parodi et al. ................. 606/191 |
| 5,346,115 | A | 9/1994 | Perouse et al. |
| 5,423,851 | A | 6/1995 | Samuels ..................... 606/198 |
| 5,522,880 | A | 6/1996 | Barone et al. ............... 128/898 |

(Continued)

FOREIGN PATENT DOCUMENTS

EP    461791 A1    12/1991

(Continued)

*Primary Examiner*—Rinaldi I. Rada
*Assistant Examiner*—Nathaniel Chukwurah
(74) *Attorney, Agent, or Firm*—Ostrolenk Faber LLP

(57) ABSTRACT

Medical methods and apparatus for locating and securing intravascular devices, substantially grafts or stents-grafts, via a laparoscopic duct created by a surgical procedure to approach a blood vessel lumen. A stapler including a tubular body having at its distal end a head with a die and die lid and at is proximal end a control mechanism with a retaining handle and a control lever pivotally thereto. The lever is operatively connected via a spring-loaded pressure rod with a fastener located in the die. The movement of lever is transformed into radial forces necessary for punching through the wall of the intravascular device and the surrounding blood vessel wall with a fastener and simultaneously bending ends of the fastener apart. Securing the ends of the intravascular device to the wall of a blood vessel is performed via a set of at least two staplers, each having several simultaneously deliverable fasteners.

18 Claims, 12 Drawing Sheets

U.S. PATENT DOCUMENTS

| | | | |
|---|---|---|---|
| 5,571,171 A | 11/1996 | Barone et al. | 128/898 |
| 5,643,208 A | 7/1997 | Parodi | 604/96.01 |
| 5,669,936 A | 9/1997 | Lazarus | 623/1.23 |
| 5,683,452 A | 11/1997 | Barone et al. | 128/898 |
| 5,693,087 A | 12/1997 | Parodi | 606/195 |
| 5,715,987 A | 2/1998 | Kelley et al. | |
| 5,720,755 A * | 2/1998 | Dakov | 606/139 |
| 5,733,325 A | 3/1998 | Robinson et al. | 623/1.11 |
| 5,843,169 A | 12/1998 | Taheri | 623/1.11 |
| 5,911,733 A | 6/1999 | Parodi | 623/1.15 |
| 5,957,940 A | 9/1999 | Tanner et al. | 606/155 |
| 5,994,750 A | 11/1999 | Yagi | 257/415 |
| 5,997,556 A | 12/1999 | Tanner | 606/153 |
| 6,004,347 A | 12/1999 | McNamara et al. | 623/23.64 |
| 6,015,431 A | 1/2000 | Thornton et al. | 612/1.14 |
| 6,030,413 A | 2/2000 | Lazarus | 623/1.11 |
| 6,102,949 A | 8/2000 | Biedermann et al. | 623/17.16 |
| 6,461,365 B2 | 10/2002 | Bolduc et al. | |
| 6,503,259 B2 * | 1/2003 | Huxel et al. | 606/153 |
| 2002/0007110 A1 * | 1/2002 | Irion | 600/170 |

FOREIGN PATENT DOCUMENTS

| | | |
|---|---|---|
| EP | 466518 A2 | 1/1992 |
| EP | 0533897 | 3/1993 |
| EP | 657147 A2 | 6/1995 |
| EP | 711135 A1 | 5/1996 |
| EP | 747020 A2 | 12/1996 |
| EP | 809980 A3 | 12/1997 |
| EP | 868154 A1 | 10/1998 |
| EP | 903118 A2 | 3/1999 |
| EP | 903119 A3 | 3/1999 |
| EP | 903120 A3 | 3/1999 |
| EP | 948945 A2 | 10/1999 |
| FR | 2746292 | 9/1997 |
| WO | 9217117 | 10/1992 |
| WO | WO 92/17117 | 10/1992 |
| WO | 01/00487 A1 | 3/2000 |
| WO | WO/0015144 A1 | 3/2000 |
| WO | WO/0019943 A1 | 4/2000 |

* cited by examiner

METHOD AND APPARATUS FOR LAPAROSCOPIC AORTIC REPAIR BY INTRAVASCULAR DEVICES

CROSS-REFERENCE TO RELATED APPLICATION(S)

The present application is a 35 U.S.C. § 371 national phase conversion of PCT/IL2005/000218 filed Feb. 23, 2005, which claims priority of Israeli Application No. 161067 filed Mar. 24, 2004.

BACKGROUND OF THE INVENTION

1. Field of the Invention

The present invention relates to medical techniques, in particular, to apparatus and methods used to prevent an aorta rupture by means of grafts or stent-grafts. More particularly, the present invention relates to methods and apparatus for securing intravascular devices, such as grafts or stent-grafts, to the walls of blood vessels in direction from the inside of these vessels towards their outer surface.

2. Description of Related Art

An aortic aneurysm (or its rupture) is a most common form of arterial aneurysms. It is a very common type of deteriorating disease affecting the ability of a lumen to conduct fluids and may be life threatening. The aortic aneurysm is a ballooning of the wall of an artery resulting from the weakening of the artery's wall due to disease or other conditions. Left untreated, the aneurysm will frequently rupture, resulting in loss of blood through the rupture, the condition, which often leads to death.

The aorta is the main artery, which supplies blood to the circulatory system. The aorta arises from the left ventricle of the heart, passes upwards and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertabrae (or the navel), where it divides into the iliac arteries. The iliac arteries, in turn, supply blood to the lower extremities and perineal region.

It is common for an aortic aneurysm to occur in that portion of the abdominal region between the renal arteries and the iliac arteries. This portion of the abdominal aorta is particularly susceptible to weakening, resulting in an aortic aneurysm. Such an aneurysm is often located near the iliac arteries. An aortic aneurysm larger than about five centimeter in diameter in this section of the aorta is ominous. Left untreated, the aneurysm may rupture, resulting in rapid, and usually fatal, hemorrhaging. Typically, a surgical procedure is not performed on aneurysms smaller than five centimeters because no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Besides synthetic grafts, there are developed and widely used all over the world particularly to prevent the rupture of aorta wall intravascular devices of the "stent-graft" type. They are inserted and located similarly to stents. The fixation of a stent-graft on the aorta walls is performed due to resilient forces of the material of the stent-graft itself usually having elastic members which bear up against the blood vessel wall or hook thereto. If the forces of resilient or elastic members of the stent-graft are insufficient for its fixation in a blood vessel, the stent-graft may be displaced from a given position and moved along the aorta due to the blood flow and peristelsic oscillations of the walls of this blood vessel, which is very dangerous to the patient.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, the common repair means is to deploy a stent-graft within the lumen of the affected aorta in the region of the aneurysm. These methods and devices have been developed to attempt to treat an aortic aneurysm without the attendant risks of intra-abdominal surgical intervention. Among them are inventions disclosed and claimed in Parodi, Juan C. et al., WO 010487A1 for Graft Device for Treating Abdominal Aortic Aneurysms and its patent family, including U.S. Pat. Nos. 5,219,355, 5,522,880, 5,571,171, 5,643,208, 5,683, 452, 5,693,087, 6,102,942, EP 461791A1, EP 809980A3, EP 903118A2, EP 903119A3, EP 903120A3 etc.

Parodi discloses a stent-graft device for locating inside an aorta affected by an aneurysm causing the aorta to have an inner diameter smaller than the sum of inner diameters of the iliac arteries. The graft has an upper main tubular portion dividing into two pending graft limbs capable of accommodating together within the restricted inner diameter of the aorta without the restriction of the aorta affecting the diameter of the limbs. The limbs have respective distal end portion with diameters larger than the diameters of the graft limbs so as to be accommodated and retained within the iliac arteries. Parodi's stent-graft is inserted using a tubular device also disclosed in his patent.

In other Parodi's patents there are disclosed stent-graft designs having a metal wire frame collapsible to a minimal size sufficient to insert the stent-graft into the artery through a puncture in its wall and expandable inside the aorta to a required size under the action of a radial force, such as a balloon. This frame is covered by a sheath which can contract and expand together with the frame under the action of external forces. Aforesaid stent-grafts are provided with means for mechanical fixation to the walls of the aorta or iliac arteries. Among those means we find balloon cuffs of a special shape at the stent-graft ends, see WO 010487A1, U.S. Pat. Nos. 5,522,880, 5,219,355, various hooks, elements shaped as scales, spirals and similar elements designed for fixation on the wall of the aorta or artery, see U.S. Pat. No. 5,911,733 Endovascular Expander of a Non-migrant Positioning, EP 948945A2 Endovascular Prosthesis with Fixation Means.

The problem of fixation of stents and stent-grafts inside the aorta and iliac arteries is PARTIALLY solved by other inventors likewise.

Lindenberg, Josef in EP 711135A1 discloses a stent with an improved anchorage in a vessel. The stent can be expanded from a radially contracted insertion state into a radially expanded positioning state such that in the radially expanded state at least one end has a larger radial extension than the remaining main body of the stent.

Samuels in U.S. Pat. No. 5,423,851 discloses a method and apparatus for affixing an endoluminal device to the walls of tubular structures within the body which utilizes incremental inflation of a balloon cuff to deploy radially projecting barbs attached to the cuff within a plurality of recesses.

Kugler, Chad disclose in their patent WO 19943A1 a stent-graft comprising radially expandable portions attached to one another and anchored to the aorta walls by a radial force. This stent-graft can bend to match the aorta longitudinal section by relative angular displacement of its portions.

Houser, Russel in WO 15144A1 discloses a system and components for treating aortic aneurysms including a reinforcing graft and combinations of fittings and rings for securing the graft to a host vessel, to branch vessels, for example, the iliac and renal arteries.

Edwin, Tarun et al., discloses in EP 868154A1 a structurally supported graft having a support structure with strain relief sections containing an internal surface, an external surface, or a wall thickness of a tubular graft member. The structural support forms a spiral about the tubular graft.

Numerous suggestions of stent-graft inventors present various hooks and anchor members, integral or not integral with the stent-graft frame to fixate the latter inside the aorta or iliac arteries. Such suggestions are disclosed in U.S. Pat. No. 6,015,431, EP 747020A2, EP 701800A1, EP 657147 A2, EP 466518A2, U.S. Pat. Nos. 5,669,936, 6,004,347, 5,733,325, 5,104,399, 6,030,413.

All the above-mentioned inventions have, in our opinion, a common drawback, which consists in the fact that the stent-grafts fixation on the inner walls of the aorta and iliac arteries is not reliable enough and brings to many complications. Therefore, under the action of blood flow and peristaltic oscillations of artery walls, stent-grafts are displaced from their proper positions, which may have grave consequences for the patient and result in his death because of the aorta rupture.

3. The Prior Art

Closest to the present invention are inventions disclosed and claimed in Taheri, Syde, U.S. Pat. No. 5,843,169 for Apparatus and Method for Stapling Graft Material to a Blood Vessel Wall while Preserving the Patency of Orifices and inventions disclosed and claimed by Tanner, Howard, in U.S. Pat. No. 5,944,750 for Method and Apparatus for the Surgical Repair of Aneurysms, U.S. Pat. No. 5,957,940 for Fasteners for Use in the Surgical Repair of Aneurysms and U.S. Pat. No. 5,997,556 for Surgical Fastener.

Taheri, Syde in U.S. Pat. No. 5,843,169 discloses an apparatus for stapling graft material to a blood vessel wall comprising a stapling device, a balloon catheter, a sheath, and an inflation means.

The apparatus design suggested by Tahery is, in our opinion, inoperative as the radial force generated by a balloon is inadequate to insert a securing member shaped as a nail into the wall of the aorta or artery. It is especially unlikely if the wall of the aorta or artery is covered with calcium plaques.

Tanner, Howard in U.S. Pat. No. 5,944,750 discloses an attachment assembly and repair graft for securing to repair a vessel having an aneurysm therein. The attachment assembly comprises an attachment cuff such that the graft is not dimensionally dependent upon the size of the vessel. The apparatus also comprises a visualization apparatus for real time direct viewing of an interior of a vessel. A penetration apparatus is disclosed for use in forming treatment specific holes in a potentially calcified vessel wall, which facilitates thereafter the securing of the graft and attachment assembly to the vessel wall. An introducer sheath device is also disclosed that comprises a sealing assembly for preventing the loss of blood from the vessel during the insertion and subsequent removal of surgical components during the surgical procedure.

In U.S. Pat. Nos. 5,957,940 and 5,997,556, H. Tanner also discloses fasteners for use during a surgical procedure for securing surgical components to a blood vessel wall under a compressive force. According to the inventions, the fastener assemblies are shaped as coiled springs or spirals or a plurality of entwined coil springs or ring type fasteners including a plurality of rings.

All the described inventions by Howard Tanner have, in our opinion, a complicated and not adequately reliable design and limited functional possibilities. So, in particular, the apparatus for setting the securing elements cannot be brought in operative position inside iliac arteries having a small lateral diameter. Because of limited space it is impossible to bend the end of the apparatus working head for setting the securing elements in the stent-graft wall. The efficiency of this apparatus for drilling holes in the walls of the stent-graft, aorta and iliac arteries is doubted, especially if these walls are calcified and covered by calcium plaques. In general, we think that the apparatus presented by Howard Tanner can be used only inside the aorta and not inside iliac arteries. As far as the suggested securing elements are concerned, we believe that their fixation in the inner walls of the aorta and iliac arteries is not reliable enough. Therefore, under the action of blood flow and peristaltic oscillations of artery walls, the stent-graft may be displaced from its proper position, which may have grave consequences for the patient and may result in his death due to the aorta rupture.

And finally, there are are known devices developed in France by Thierry Richard, Eric Perouse, such as "Surgical staple inserter", see U.S. Pat. No. 5,346,115; WO 9217117; EP 0533897 and "Surgical staple for tissue", see Pat. FR 2746292.

U.S. Pat. No. 5,346,115; WO 9217117; EP 0533897 describes a surgical staple inserter for joining two ducts such as a blood vessel and blood prosthesis. The staple inserter ejects staples in a radial direction relative to the axis of the ducts. In one embodiment, it includes a staple holder surrounded by the prosthesis and containing a series of staples arranged in at least one ring. All the staples are ejected simultaneously. The staple inserter also includes an anvil outside the organic duct, and a device for spacing apart the anvil and the staple holder in relation to their relative working position. Projections hold the prosthesis in place during the insertion of the staple holder into the ducts.

One of the drawbacks of this device is the complexity of its design, but its chief drawback is that it does not allow to bend the ends of staples when they are extending from the device body outwardly, through the prosthesis and the blood vessel wall. Therefore it is necessary to provide the device with anvils arranged outside the operated blood vessel, and this makes both the device itself and the whole operation for setting a stent-graft more complicated and expensive.

Pat. FR 2746292 describes a surgical staple having a circular spiral formed of metallic wire. It extends on a complete spiral, which is augmented over part of its length. The staple can have a barbed end. The device for this staples insertion comprises a guide tube, extending towards the front by an inwardly curved section with a guide channel. At least a section of metal wire moves in the guide tube. A pusher moves the wire section towards the distal end of the guide tube.

The device has several drawbacks. It is rather difficult to set the staples as the device must be positioned very accurately relative to the prosthesis wall, it is impossible to set several staples simultaneously, and considerable projection of parts of staples inside the prosthesis may result in an accelerated thrombogenesis in this prosthesis lumen.

On the whole, today no methods and apparatus for grafts and stent-grafts fixation to the walls of a blood vessel from inside this vessel, that are developed, brought to mass production and use in real practice, are known to the authors of the present invention.

An object of the present invention is to provide reliable and relatively simple means for securing a graft, stent-graft or other intravascular devices to the wall of the aorta, iliac arteries or other arteries, in particular, a new and improved method for stapling and a stapling apparatus based on this method.

Another object of the present invention is to provide suturing of a prosthesis to a blood vessel over the whole perimeter of connection, as well as security and tightness of this connection even in such hard to reach spots, as the aorta neck or in the area immediately under renal arteries.

SUMMARY OF THE INVENTION

The present invention includes a method for intraluminal fixation of intravascular devices, such as grafts or stent-grafts.

The method includes several successive steps. At the first step a special stapler is prepared for the operation. For this purpose there is checked the state of its loading with fastener means (loaded or unloaded) and, if necessary, it is being loaded. Then a corresponding intravascular device, substantially graft or stent-graft, is fitted over this stapler body, with partial reversing, if necessary, of one end of this intravascular device. Thereupon the fitted intravascular device is secured on the stapler body via a means for its temporary fixation. At the next stage there is created, by a surgical procedure, a duct for approaching the lumen of an operated blood vessel, substantially the aorta, directly through the wall of this blood vessel. Then, through the duct thus opened there is inserted into the lumen of the operated blood vessel, substantially the aorta, a special stapler with a corresponding intravascular device, substantially graft or stent-graft, fitted over and secured thereon, and this intravascular device is located in a required position. Thereafter the stapler is brought into operative position necessary for securing the first end of the intravascular device, in this case a graft, to the wall of a blood vessel, substantially the aorta. Then the matching of mutual location of the first end of this intravascular device, the place of its supposed securing to the blood vessel wall, as well as the stapler actuator with fastener means located near its free end.

Then in the stapler actuator there are generated radial forces sufficient to act on fastener means. Due to this force fastener means extend from the actuator radially, punch the wall of the intravascular device in such a way that the distal ends of these fastener means are partly outside the blood vessel and are bent over on its outer surface to form a rigid connection of the first end of this intravascular device with the blood vessel wall. Then the stapler actuator is moved clear of the first end of the wall of this intravascular device, so that the fastener means remain fixed in the wall of this intravascular device and in the blood vessel wall to secure the first end of this intravascular device with a corresponding blood vessel portion and prevent thereby any its displacement relative to this blood vessel. Next the stapler is brought into inoperative position necessary for its free removal and removed from the intravascular device and from the blood vessel.

At the next step in the intravascular device (graft or stent-graft) there is made an incision to approach its lumen. Then another special stapler for securing the second end of the intravascular device to the wall of a given blood vessel (aorta) is inserted via a previously made duct and via the incision into the lumen of this intravascular device (graft or stent-graft). This stapler is brought into operative position whereupon its actuator with fastener means located in the die at its free end is brought to the wall of the intravascular device, at the spot of its second end connection with the blood vessel wall. Then there is checked the matching of positioning of the second end of this intravascular device, the place of its supposed securing to the blood vessel wall, as well as of the stapler actuator with fastener means. At generating in this stapler actuator an axial force sufficient to act on fastener means these fastener means extend from the actuator in radial direction, punch the wall of this intravascular device and surrounding blood vessel wall in such a way that the distal ends of these fastener means partly come outside the blood vessel and are bent over on its outer surface to form a rigid connection of the second end of this intravascular device with the blood vessel wall. Then the actuator of the other stapler is moved clear of the wall of this intravascular device, whereby fastener means remain fixed in the wall of this intravascular device and in the blood vessel wall to secure the second end of this intravascular device with a corresponding portion of the blood vessel and prevent thereby any its displacement relative to this blood vessel. Then the stapler is brought into inoperative position necessary for its free removal from the intravascular device and removed therefrom and from the blood vessel.

At the last step, by a surgical procedure, there are closed the incision in this intravascular device and the duct to approach the lumen of the intravascular device and the blood vessel lumen.

Owing to the above manipulations there is created a secure multiple-spot connection of the intravascular device with the blood vessel wall which prevents the displacement of this intravascular device from an assigned position due to blood flow and peristelsic oscillations of the blood vessel wall.

According to the claimed method, it is possible to secure an intravascular device, such as graft or stent-graft, to a blood vessel wall via at least one suggested stapler and using at least two fastener means simultaneously more than at two points. This is performed substantially near one of the free ends of this intravascular device.

According to the suggested method, it is also possible to secure the ends of an intravascular device, such as a stent-graft, having a broad proximal part and bifurcated distal part to the wall of a blood vessel (the aorta), via a set of at least two staplers and using in each of them simultaneously at least two fastener means. The set contains at least one first stapler for securing the broad proximal part of a stent-graft with the aorta wall and at least one second stapler for securing the bifurcated part of this stent-graft to the aorta wall. The proximal end of a stent-graft having a broad proximal part is secured to the wall of a blood vessel (aorta) in the aorta neck area via the first of staplers comprised in the stapler set and using simultaneously at least two said fastener means.

The distal end of a stent-graft having a bifurcated distal part is secured to the aorta wall via the second of staplers comprised in the set and using simultaneously at least two fastener means. This is performed near the free end of the first or second branches of the bifurcated distal part of this stent-graft.

At last, according to the claimed method, the stent-graft may be secured to the aorta wall using at least two fastener means near the free end of both branches of the bifurcated distal part of this stent-graft.

The claimed invention also includes a stapler for laparoscopic aortic repair by intraluminal fixation of intravascular devices, substantially grafts or stent-grafts. This stapler comprises: a tubular body, a head with a die and die lid disposed at one end of the tubular body, as well as a control mechanism mounted at the opposite end of this tubular body, a pressure rod located within the latter and, at last, means for transmitting axial force from the pressure rod to fastener means and for temporary fixation of delivered intravascular devices on the stapler body.

The stapler tubular body is adapted for positioning within a blood vessel and is rigid in longitudinal direction and flexible in lateral direction.

The stapler head, substantially of cylindrical shape, is disposed at the free end of the tubular body and has an inner axial cavity proximal end and distal end. At the proximal end of this head there are rigidly secured a die and die lid aligned with this head and with one another.

The die serves for locating fastener means, substantially U-shaped staples. It is shaped substantially as a barrel having a proximal end, distal end, substantially cylindrical generatrix and an inner axial cavity which is open on the side of barrel distal end and terminates in a bottom at the proximal end of this barrel. This bottom has a through axial hole, through, evenly arranged radial slots, and on its end face presented to the die lid—recesses with grooves for locating fastener means, substantially U-shaped staples. These recesses with grooves are coaxial with radial slots and provided with means for setting apart the ends of U-shaped staples which are disposed along the groove axes, immediately adjacent to the die generatrix and are substantially V-shaped.

The die lid has a substantially cylindrical generatrix, proximal and distal end faces, radial slots evenly arranged in the body of this die lid near its distal end face and extending onto its cylindrical generatrix, as well as means for retaining the free ends of U-shaped staples and means for separating from the stapler the middles of these U-shaped staples at the end of their working stroke. All these means are disposed near the points of intersection of radial slots with the distal end face and cylindrical generatrix of this die lid.

The control mechanism is disposed at the tubular body end opposite to the head and includes a substantially cylindrical hollow body with a proximal end and a distal end with a retaining handle extending from the body at a certain angle, from about 30 degrees to about 90 degrees and a control lever pivotally mounted on this retaining handle.

The pressure rod is located within the hollow body. It has a longitudinal axis, a proximal end and a distal end. This pressure rod is rigid in longitudinal direction and flexible in lateral direction and is operatively associated via its distal end with the control lever, and its proximal end is substantially conical and is disposed in the inner axial cavity of the die to reciprocate relative to the latter.

Means for transmitting axial force from the pressure rod to fastener means, substantially U-shaped staples, and for converting this axial force into radial forces applied to each of these U-shaped staples, are disposed substantially in the inner axial cavity of the die to periodically cooperate with the proximal end of the pressure rod.

The stapler also has a means for temporary fixation on its body of intravascular devices, substantially grafts or stent-grafts located on this stapler body outside.

The stapler control mechanism has a substantially cylindrical hollow body with a proximal end, a distal end and retaining handle extending sidewise therefrom at a certain angle, from about 30 degrees to about 90 degrees, the handle being provided with a swing lock and control lever pivotally attached to this handle. The control lever has a pressure end movably secured within the hollow body in the clearance between the spring-loaded end of the pressure rod and an adjusting screw aligned with this pressure rod.

The die for receiving fastener means is shaped as a barrel with a substantially cylindrical generatrix and an inner axial cavity open on the side of the barrel distal end and terminating in a bottom at the proximal end of this barrel. The die has through, evenly arranged radial slots on its bottom, and on the end face of this bottom facing the die lid—recesses with grooves for receiving fastener means, substantially U-shaped staples, with means for setting apart the ends of the latter. These recesses with grooves have substantially equal depth relative to the end face of die bottom and are aligned with the radial slots. They may also have different depth relative to the end face of die bottom, but even in this case they are also aligned with the radial slots. The recesses with grooves may have at least two different depths relative to the end face of die bottom, recesses with grooves of different depths alternate with one another.

The fastener means are shaped substantially as U-shaped staples and disposed radially in the grooves of stapler die to extend radially from these grooves due to radial forces. The free ends of U-shaped staples are located on both sides of means for setting apart the ends of these fastener means disposed along the axes of grooves, immediately adjacent to the die cylindrical generatrix and are substantially V-shaped.

Means for setting apart the ends of fastener means, substantially U-shaped staples, are disposed along the axes of grooves, immediately adjacent to the cylindrical generatrix of the die and are substantially V-shaped, with lateral faces which are substantially curvilinear or radial, concave and diverging from one another in direction from the center of this die to its cylindrical generatrix, which allows to bend outwardly the free ends of fastener means during their extension from the die due to said radial forces.

The die lid is provided with means for retaining the free ends of fastener means, substantially U-shaped staples, containing springy members disposed in the lid near the intersection points of radial slots with the distal end face and cylindrical generatrix of this die lid.

The die lid is further provided with means for separating from the stapler the middles of fastener means, substantially U-shaped staples, at the end of their working stroke. These means contain recesses located near intersection points of radial slots with the distal end face and cylindrical generatrix of this die lid. Besides, the die lid is made of a transparent material to check the state of fastener means, substantially U-shaped staples.

The pressure rod has a longitudinal axis, a substantially conical proximal end, a distal end and a thrust collar near its distal end. This pressure rod is rigid in longitudinal direction and flexible in lateral direction. The pressure rod is spring-loaded, operatively associated via its distal end with the control lever and disposed so as to reciprocate, by its distal end—within the hollow body of said control mechanism, and by its substantially conical proximal end—within the inner axial cavity of the die. The pressure die has a substantially conical proximal end with a cone vertex angle from about 3 degrees to about 35 degrees. The value of this angle is substantially defined from about 10 degrees to about 20 degrees.

The means for transmitting axial force from the pressure rod to fastener means, substantially U-shaped staples, and for converting this axial force into radial forces applied to each of these U-shaped staples contains curved L-shaped levers pivotally secured via the end of its long arm and evenly arranged in the inner axial cavity of the die in such a way that their short arms bent outwardly relative to the die longitudinal axis are located in corresponding through radial slots on this die bottom, the bent L-shaped levers capable of periodical cooperation by inner faces of their long arms with the substantially conical proximal end of the pressure rod, and by their free ends of outwardly bent short arms—with the middles of corresponding U-shaped staples. Curved L-shaped levers are pivotally mounted via the ends of their long arms on a ring located within the inner axial cavity of the die, in the clearance between the head free end and inner ribs of this die extending from the wall of its inner axial cavity towards the die longitudinal axis. The ribs have evenly arranged radial slots each of them receiving a corresponding movable curved L-shaped lever.

The die, die lid and fastener means, substantially U-shaped staples, located in die grooves form in combination a single set of the stapler actuator which is configured to be removed from the stapler body with following replacement by other, similar interchangeable sets.

The means for temporary fixation on the stapler body of delivered intravascular devices, substantially grafts or stent-grafts, located on this stapler body outside substantially contains an adjusting screw with a thrust head located in the distal part of control mechanism body, coaxially with the pressure rod and on the other side of the pressure end of control lever, as well as fastener means, substantially U-shaped staples, with which this adjusting screw is operatively connected via the pressure end of control lever and pressure rod.

BRIEF DESCRIPTION OF THE DRAWINGS

The invention will now be described in conjunction with the following drawings in which like reference numerals designate like elements and wherein.

DETAILED DESCRIPTION OF PREFERRED EMBODIMENTS

Figure 1:
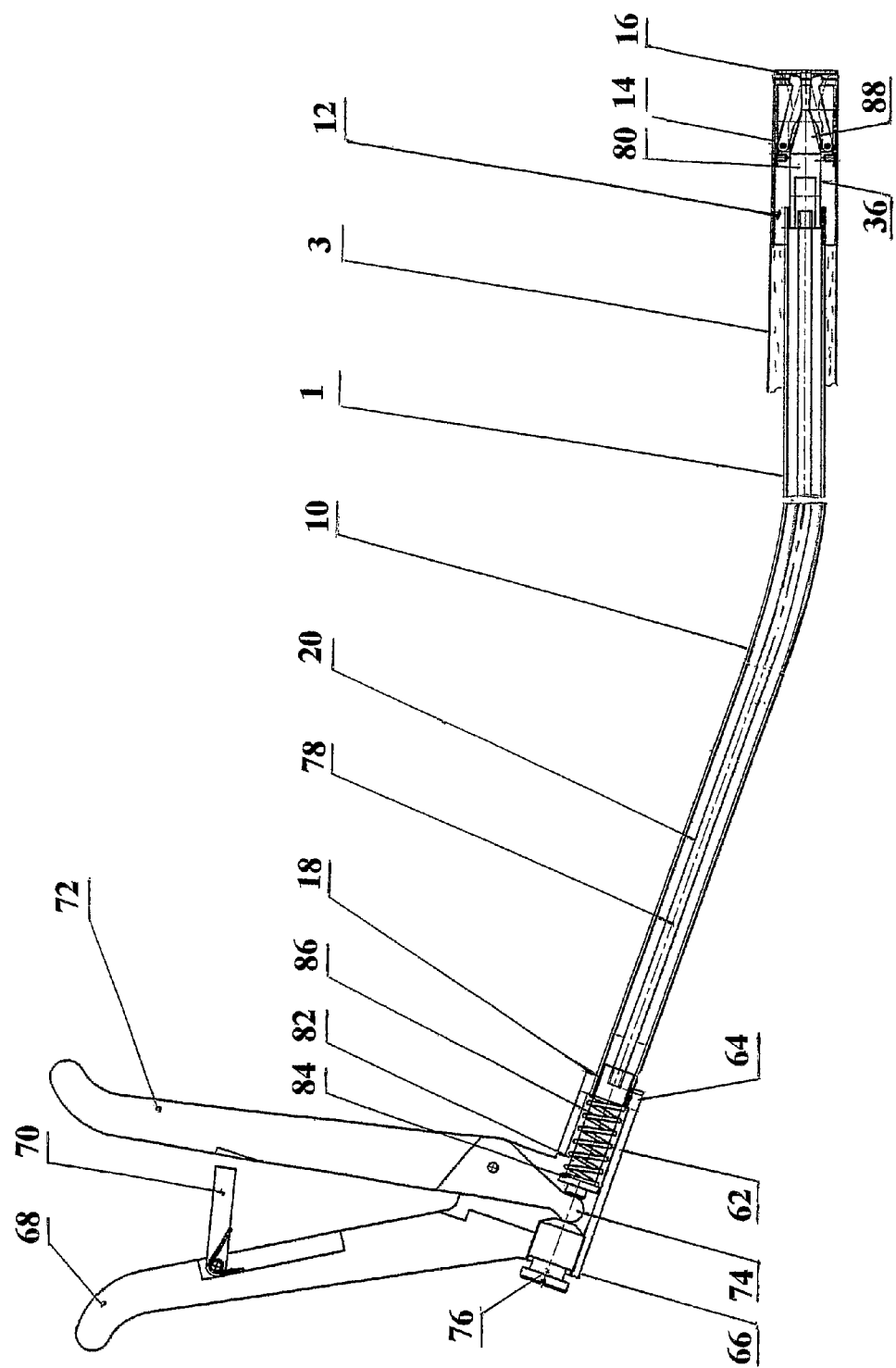
FIG. 1 shows a longitudinal section of the stapler according to the first embodiment of the present invention.

The following descriptions of the preferred embodiments of the present invention are described. The inventors of the present subject matter contemplate that the embodiments described herein are capable of use in the repair of other vessels and in other procedures. Thus, it is intended that the present invention cover the modifications and variations of the invention, provided they come within the scope of the appended claims and their equivalents.

The most preferable embodiments of the stapler according to the present invention are shown in drawing FIG. 1-10.

The claimed invention (FIG. 1) includes stapler 1 for laparoscopic aortic repair by intraluminal fixation of intravascular devices, substantially grafts or stent-grafts 3.

Stapler 1 comprises (FIG. 1): a tubular body 10, head 12 with die 14 and die lid 16 located at one end of tubular body 10, as well as control mechanism 18 mounted at the opposite end of tubular body 10. Tubular body 10 of stapler 1 is adapted to be positioned within a blood vessel and is rigid in longitudinal direction and flexible in lateral direction. Tubular body 10 encloses pressure rod 20.

Figure 2:
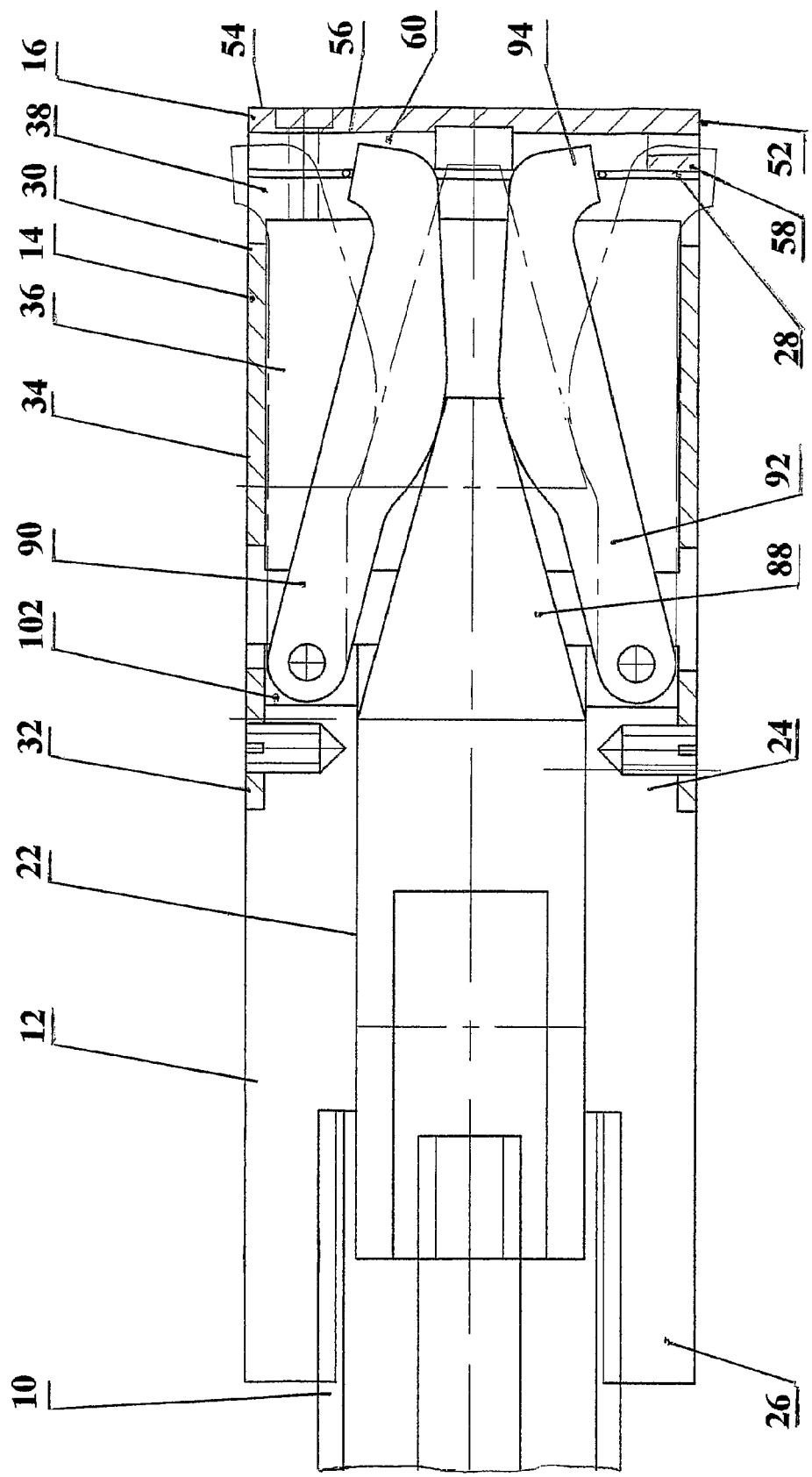
FIG. 2 shows a longitudinal section of the stapler head and die according to the first embodiment of the present invention.
Figure 3:
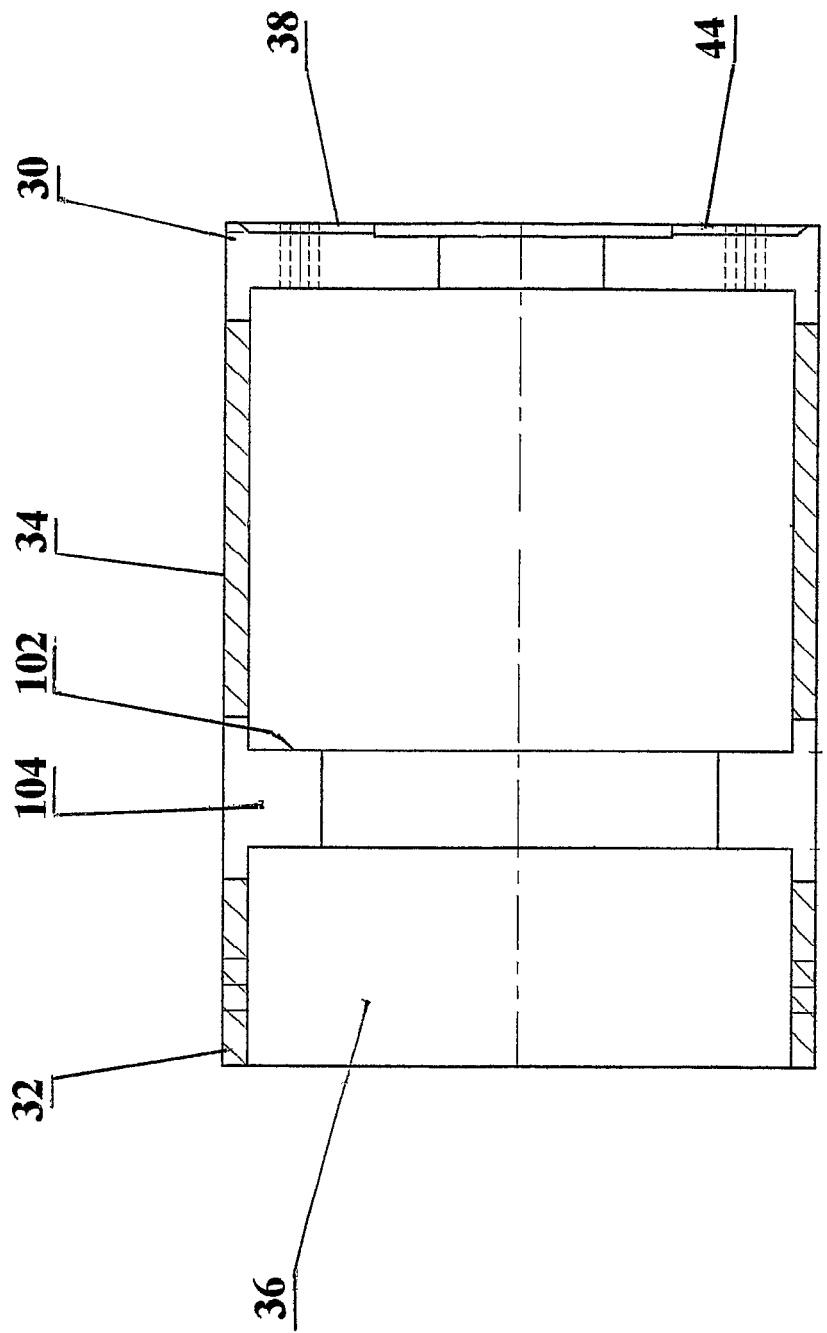
FIG. 3-5 show the first embodiment of the stapler die—its longitudinal section, front view and a groove close-up.
Figure 4:
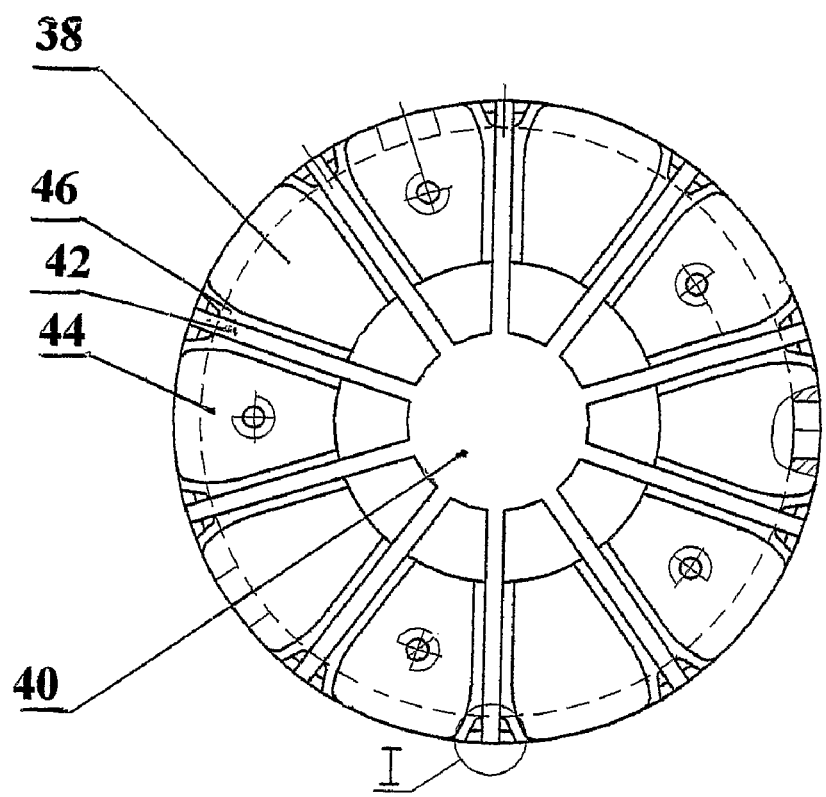

Substantially cylindrical head 12 of stapler 1 is disposed at the free end of tubular body 10 (FIGS. 1, 2) and has an inner axial cavity 22, proximal end 24 and distal end 26 (FIG. 2). At the proximal end 24 of head 12 there are rigidly secured die 14 and die lid 16 coaxial with this head 12 and with one another.

Figure 5:
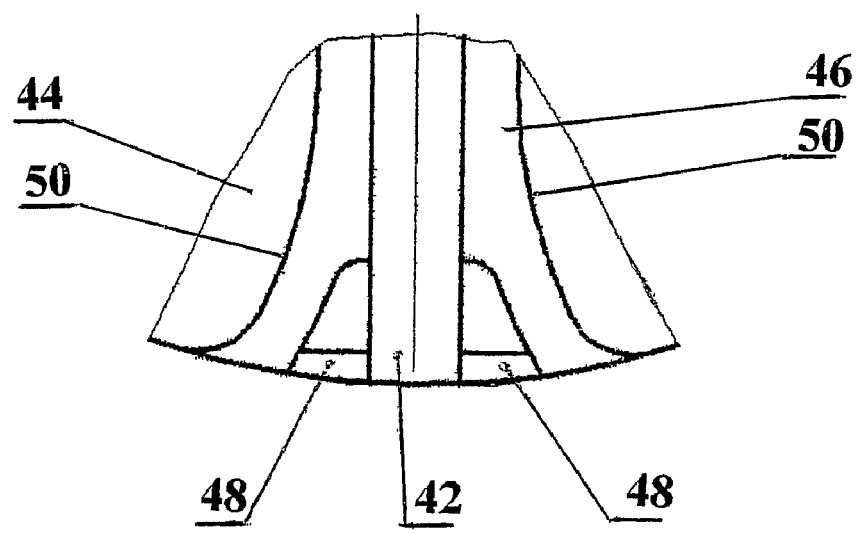
Figure 6:
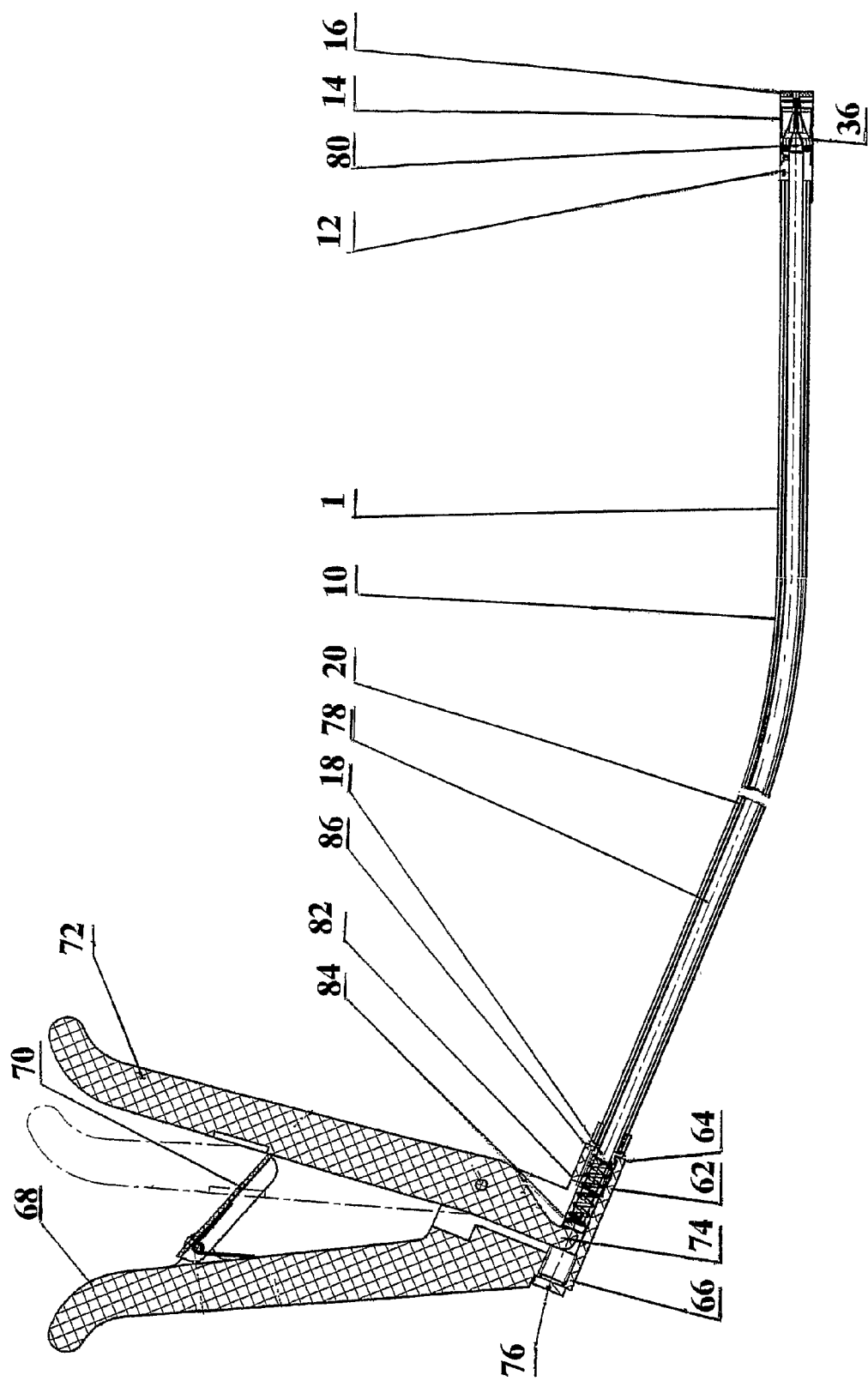
FIG. 6 shows a longitudinal section of the stapler according to the second embodiment of the present invention.
Figure 7:
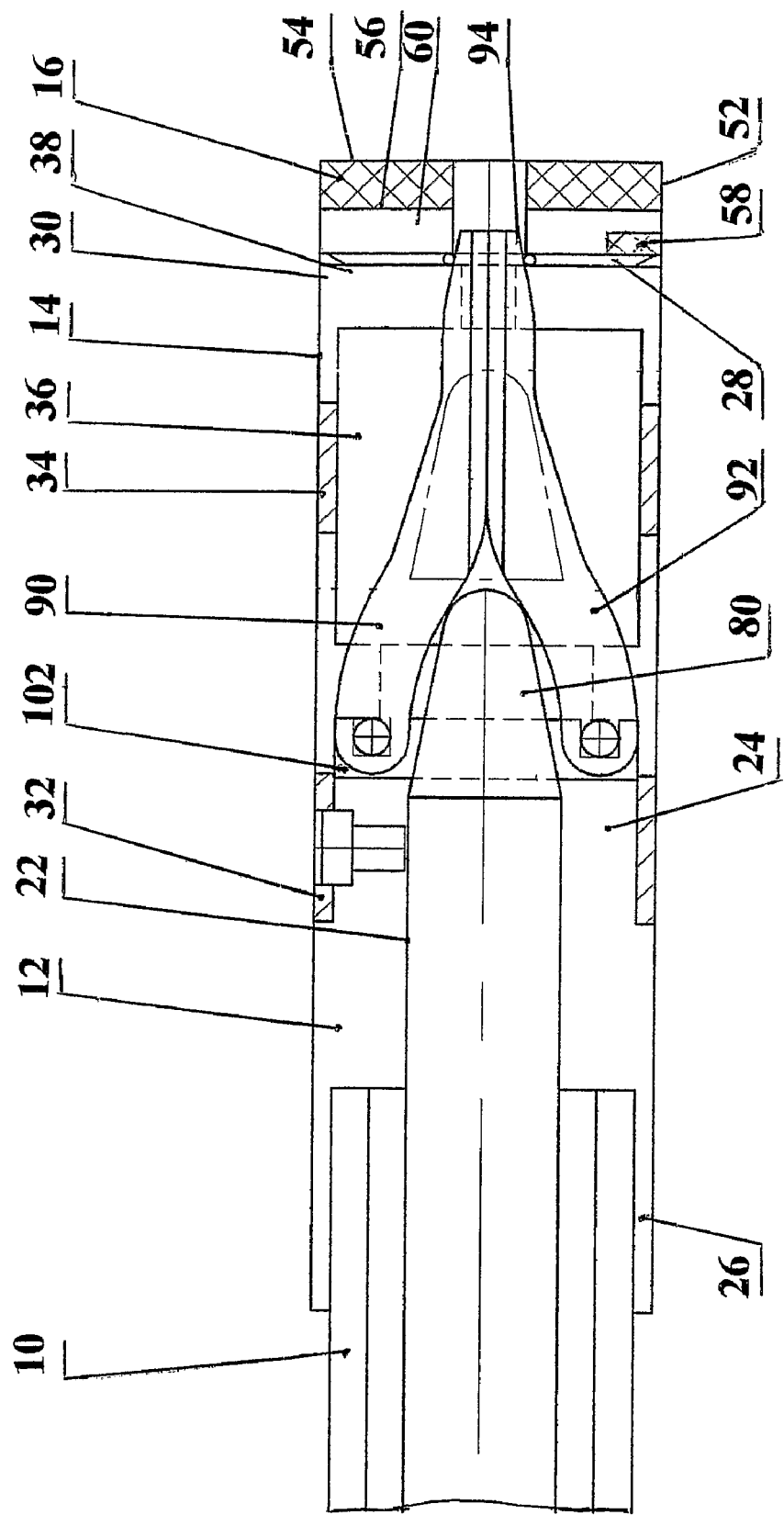
FIG. 7 shows a longitudinal section of stapler head and die according to the second embodiment of the present invention.
Figure 8:
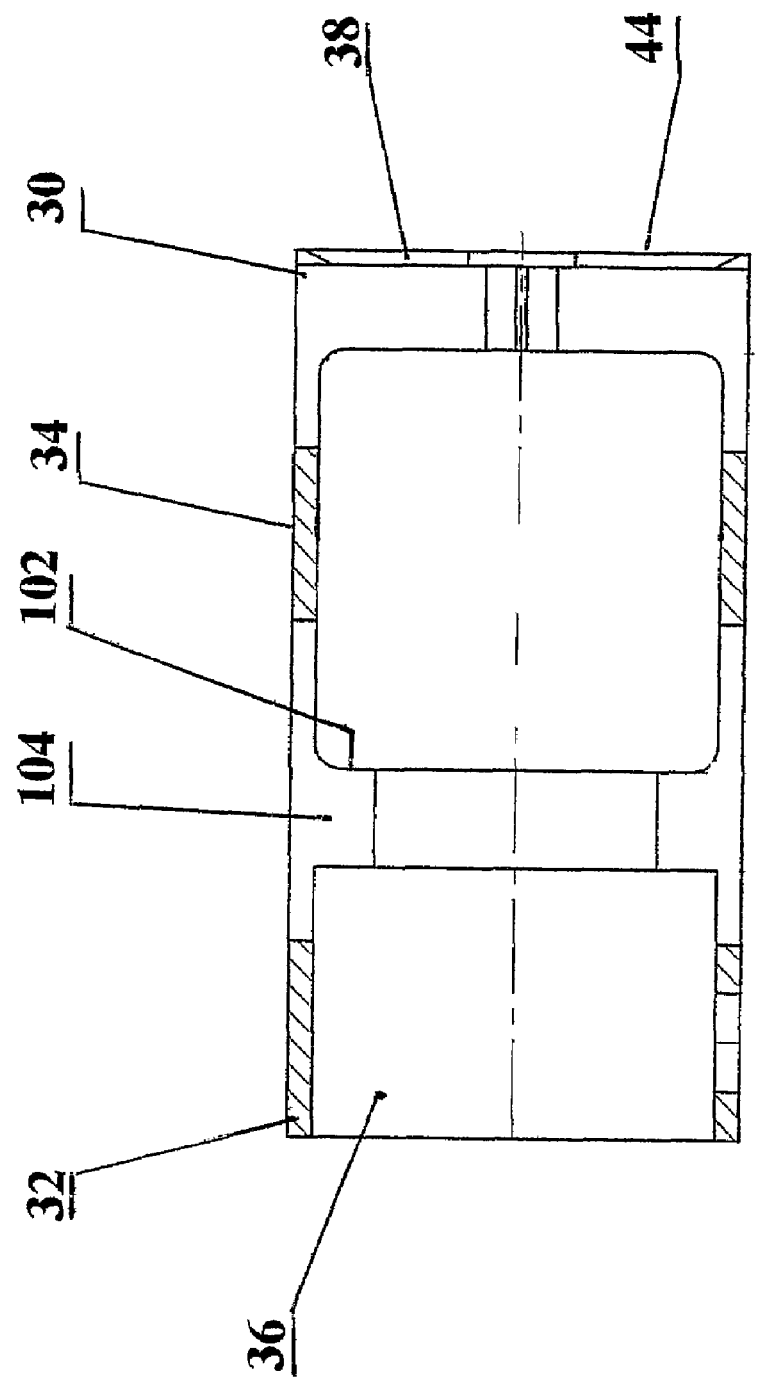
FIG. 8-10 show the second embodiment of the stapler die—its longitudinal section, front view and a groove close-up.
Figure 9:
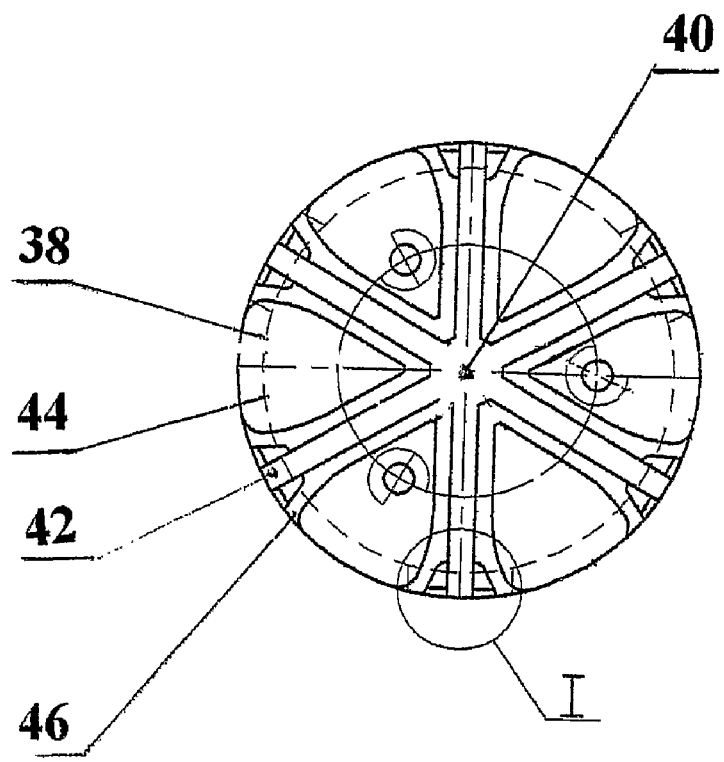
Figure 10:
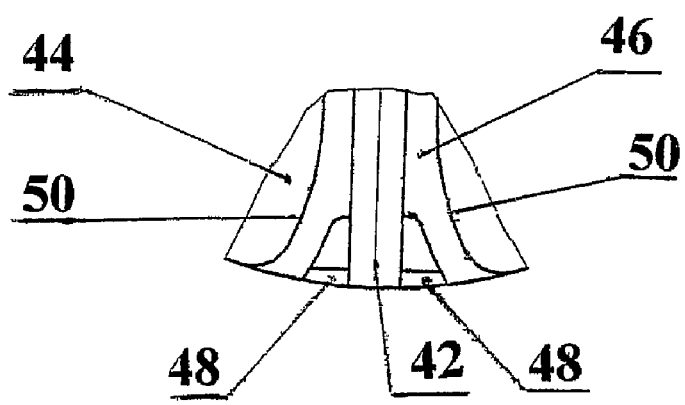

Die 14 serves for receiving fastener means, substantially U-shaped staples 28 (FIG. 2). Die 14 is shaped substantially as a barrel having a proximal end 30, distal end 32, substantially cylindrical generatrix 34 and inner axial cavity 36 open on the side of the distal end 32 of the barrel and terminating in bottom 38 (FIGS. 2, 3) at the proximal end 30 of the barrel. This bottom 38 has a through axial hole 40 (FIGS. 3, 4, 5), through, evenly arranged radial slots 42, and on its end face 44 presented to die lid 16—recesses with grooves 46 for receiving fastener means, substantially U-shaped staples 28. These recesses with grooves 46 are coaxial with radial slots 42 and provided with means for setting apart the ends of U-shaped staples—bulges 48 which are disposed along the axes of grooves 46, immediately adjacent to generatrix 34 of die 14 and substantially V-shaped (FIG. 5). Bulges 48 are substantially V-shaped, with lateral guiding faces 50 which are substantially curvilinear or radial, concave and diverging from one another in direction from the center of said die 14 to its cylindrical generatrix 34.

Recesses with grooves 46 have substantially the same depth relative to end face 44 of the bottom of die 14 and are coaxial with radial slots 42. They may also have a different depth relative to end face 44 of the bottom of die 14, but they are also coaxial with radial slots 42. In another embodiment of die 14 recesses with grooves 46 have at least two different depths relative to end face 44 of the bottom of die 14, recesses with grooves 46 of different depths are arranged alternately with one another.

Fastener means, substantially U-shaped staples 28, are disposed radially in grooves 46 of die 14 of stapler 1 to extend radially from these grooves 46 due to radial forces. The free ends of U-shaped staples 28 are located on both sides of means for setting apart these fastener means—bulges 48 disposed along the axes of grooves 46, immediately adjacent to cylindrical generatrix 34 of die 14 and substantially V-shaped.

Lid 16 of die 14 has a cylindrical generatrix 52, proximal 54 and distal 56 end faces, as well as radial slots evenly arranged in the body of lid 16 near its distal end face 56 and extending onto its cylindrical generatrix 52. Besides, lid 16 is provided with means for retaining the free ends of U-shaped staples 28 and means for separating from the stapler the middles of these U-shaped staples 28 at the end of their working stroke. All these means are located near the points of intersection of radial slots 42 with distal end face 56 and cylindrical generatrix 52 of this lid 16. Means for retaining the free ends of fastener means, substantially U-shaped staples 28, contain cantilever springy members 58 (FIG. 2) created in the body of lid 16 by cutting therein weakening slots 42 and located near the points of intersection of radial slots 42 with distal end face 56 and cylindrical generatrix 52 of this lid 16.

Lid 16 is also provided with means for separating from stapler 1 the middles of fastener means, substantially U-shaped staples 28 at the end of their working stroke. These means are shaped as recesses 60 located near the points of intersection of radial slots 42 with distal end face 56 and cylindrical generatrix 52 of this lid 16 (FIG. 2). Besides, lid 16 is made of a transparent material for checking the state of fastener means, substantially U-shaped staples 28.

Die 14, lid 16 and fastener means, substantially U-shaped staples 28 located in grooves 46 of die 14 form in combination a single set of the actuator of stapler 1 which is configured to be removed from stapler 1 and replaced by other, similar interchangeable sets (FIG. 2).

Control mechanism (FIG. 1) 18 is located at the opposite to head 12 end of tubular body 10 and includes a substantially cylindrical hollow body 62 with proximal end 64 and distal end 66 with a retaining handle 68 provided with a swing lock 70 and control lever 72 pivotally mounted on this handle. This handle extends from distal end 66 sidewise at a certain angle, from about 30 degrees to about 90 degrees. Control lever 72 has a pressure end 74 movably mounted within hollow body 62 in the clearance between spring-loaded end of pressure rod 20 and adjusting screw 76 coaxial with this pressure rod 20.

Pressure rod 20 (FIG. 1) is located within hollow body 10. It has a longitudinal axis 78, proximal end 80, distal end 82 and thrust collar 84 near its distal end 82. This pressure rod 20 is rigid in longitudinal direction and flexible in lateral direction. Pressure rod 20 is loaded with a spring 86, operatively associated via its distal end 82 with control handle 72 and capable of reciprocating, by its distal end 82—within hollow body 62 of control mechanism 18, and by its substantially conical proximal end 80—in inner axial cavity 36 of die 14. Pressure rod 20 has a substantially conical proximal end 80 (or tip 88, as shown in the first embodiment of the stapler) with a cone vertex angle from about 3 degrees to about 35 degrees. The value of this angle is defined from about 10 degrees to about 20 degrees.

Figure 11:
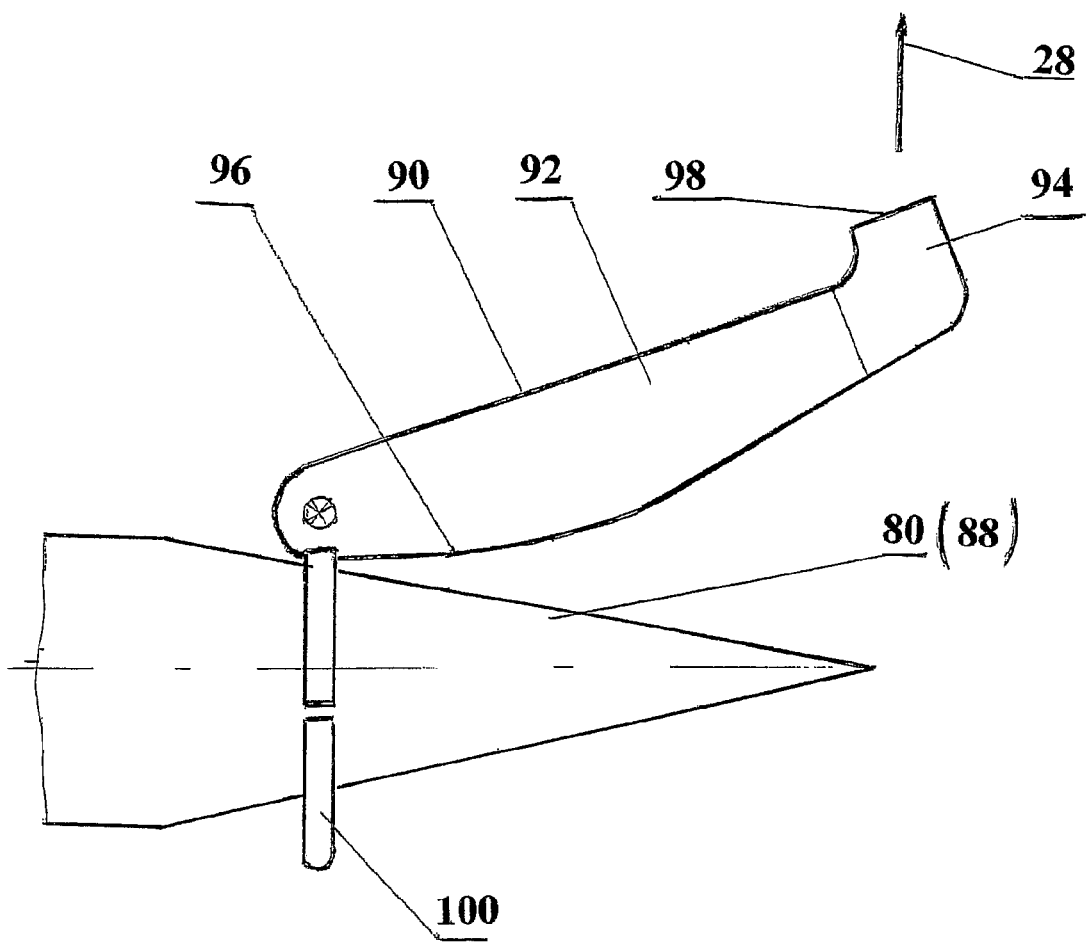
FIG. 11 shows an L-shaped lever and diagram of its cooperation with the pressure rod.
Figure 12:
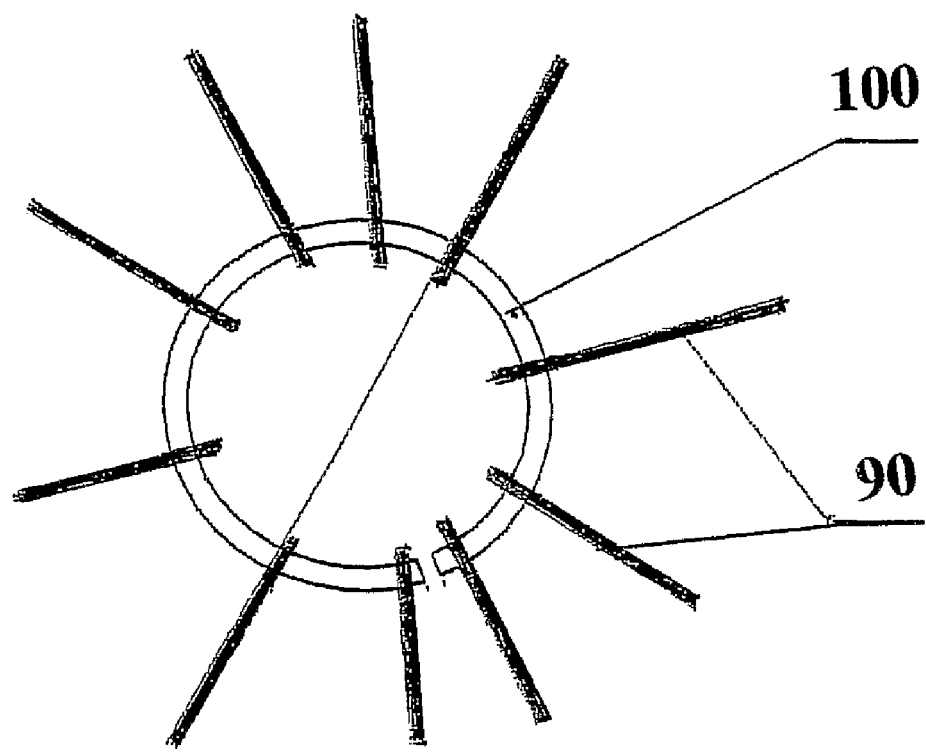
FIG. 12 shows a diagram of L-shaped levers securing on a ring.

Means for transmitting axial force from pressure rod 20 to fastener means, substantially U-shaped staples 28, and for converting this axial force into radial forces applied to each of these U-shaped staples 28 are located substantially in inner axial cavity 36 of die 14 for periodical cooperation with the proximal end of pressure rod 20. Means for transmitting axial force contain curved L-shaped levers 90 (FIGS. 2, 11, 12) pivotally mounted by the end of their long arms 92 in the inner axial cavity of die 14 in such a way that their short arms 94 bent outwardly relative to the longitudinal axis of the die are disposed in corresponding through radial slots 42 on bottom 38 of this die 14, and curved L-shaped levers 90 are configured to periodically cooperate via inner faces 96 of their long arms 92 with a substantially conical proximal end of pressure rod 80 (or tip 88), and via their free ends 98 of outwardly bent short arms 94—with the middles of corresponding U-shaped staples 28. Curved L-shaped levers 90 are pivotally mounted via the ends of their long arms 92 on ring 100 (FIGS. 2, 11, 12) located in inner axial cavity 36 of die 14, in the clearance between the free end of head 12 and inner ribs 102 of this die 14 extending from the wall of its inner axial cavity 36 towards the longitudinal axis of die 14. Ribs 102 have evenly arranged radial slots 104 (FIG. 3) each of them receiving a movable corresponding curved L-shaped lever 90.

Stapler 1 also has a means for temporarily fixating on its body the delivered intravascular devices, substantially grafts or stent-grafts 3, located on this body of stapler 1 outside. This means is substantially an adjusting screw 76 (FIG. 1) with a thrust head disposed in distal part 66 of body 62 of control mechanism 18, coaxially with rod 20 and on the other side of pressure end 74 of control lever 72, as well as U-shaped staples 28 wherewith this adjusting screw 76 is operatively associated via pressure end 74 of control lever 72 and pressure rod 20.

All staplers 1 set forth hereinabove relate to its first embodiment, that is to a stapler serving substantially for delivering a graft or stent-graft and its fixation in the aorta neck. The second embodiment of the stapler has exactly the same design and differs from the first embodiment solely in a smaller diameter of head 12, die 14 and lid 16, as well as in a smaller number of U-shaped staples 28 located therein, as it is intended for fixation of graft or stent-graft 3 in bifurcations with a smaller lumen. Besides, in the second embodiment of stapler 1 there is slightly changed the form of curved L-shaped levers 90, but they perform their functions exactly in the same way as corresponding levers 90 in the first embodiment of stapler 1. Therefore all, design elements of the second embodiment of the stapler shown in FIG. 6-10 have the same reference numerals as corresponding design elements according to the first embodiment shown in FIG. 1-5.

Figure 13:
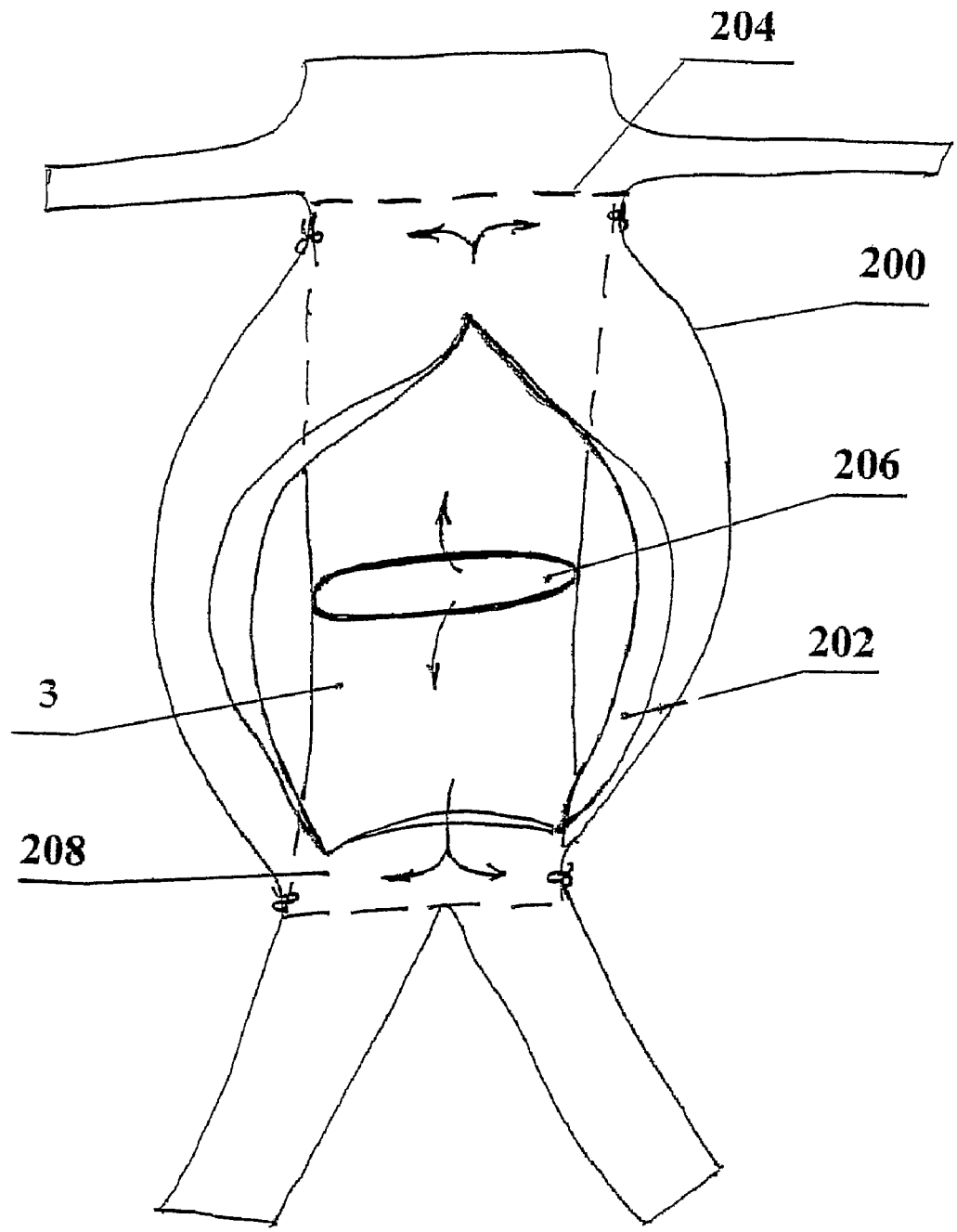
FIG. 13-14 show diagrams of locating a graft or stent-graft using a set of claimed staplers.
Figure 14:
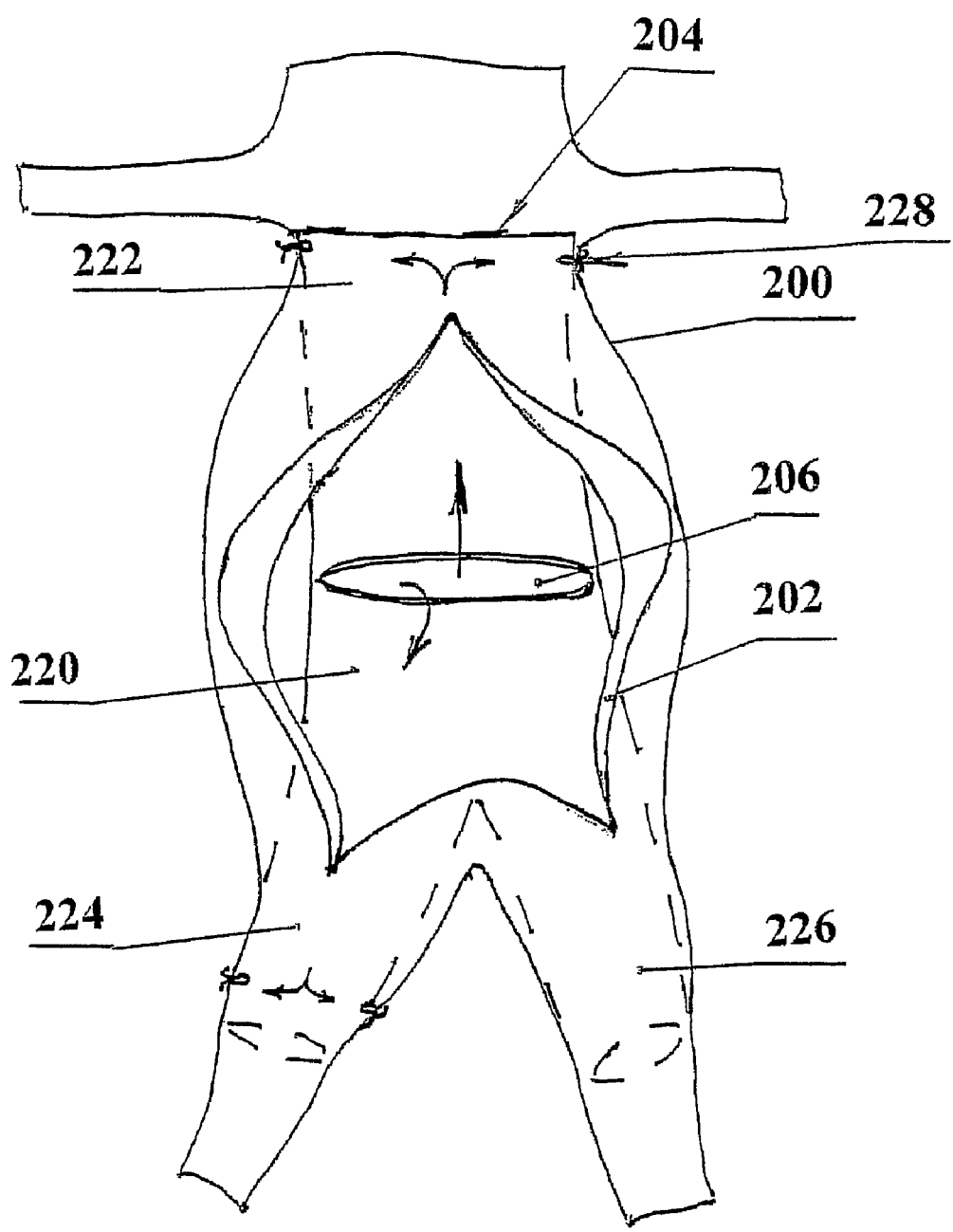

Besides stapler 1, the present invention includes a method for securing an intravascular device, such as graft or stent-graft 3, to the wall of a blood vessel, substantially aorta 200 (FIGS. 13, 14).

Let us consider, by way of example, the claimed method for securing an intravascular device using claimed stapler 1 for securing graft 3. The method includes several successive steps (FIG. 13). At the first step special stapler 1 is prepared for the surgical procedure. To this end there is checked the state of its loading with fastener means—U-shaped staples 28 (loaded or unloaded), and, if necessary, it is loaded. Then there is fitted over head 12 with die 14 and body 10 of this stapler 1 a corresponding intravascular device, substantially graft or stent-graft 3, with partial reversing, if necessary, of one end of this intravascular device. Graft 3 located on stapler 1 is fixated thereon via adjusting screw 76. By driving in this adjusting screw 76 pressure end 74 of control lever 72 and pressure rod 20 are acted upon. As a result, U-shaped staples 28 slightly extend from die 14, prick by their pointed ends graft 3 to fix temporarily its position on die 14 of stapler 1. Stapler 1 is ready for work.

At the next stage there is created by surgical procedure duct 202 to approach the lumen of an operated blood vessel, substantially aorta 200, directly through the wall of this blood vessel (aorta). Then, through thus opened duct 202, there is inserted into the lumen of an operated blood vessel, substantially aorta 200, a special stapler 1 (FIG. 13) with an intravascular device, substantially graft 3 fitted thereover, and this graft 3 is located in a necessary place within aorta 200. Then stapler 1 is brought into operative position necessary for securing the first end of an intravascular device, in this case graft 3, to the wall of a blood vessel, substantially aorta 200. Thereafter there are checked the matching of mutual location of the first end 204 of graft 3, the place of its supposed securing to the wall of aorta 200, as well as of the actuator of stapler 1 with fastener means—U-shaped staples 28 located in die 14 at its free end.

Then, in the actuator of stapler 1 there is generated an axial force sufficient for acting on fastener means—U-shaped staples 28. Due to this force U-shaped staples 28 extend further from die 14 in radial direction, punch not only the wall of intravascular device—graft 3, but also the surrounding wall of aorta 200 in such a way, that the distal ends of these U-shaped staples 28 extend in part outside aorta 200 and are bent over on its outer surface to form a rigid connection of first end 204 of graft 3 with the wall of aorta 200. Next, the actuator of stapler 1 is moved clear of the first end of aorta 200 wall, so that U-shaped staples 28 remain fixed in the wall of graft 3 and in the wall of aorta 200 to secure the first end of graft 3 to a corresponding portion of aorta 200 and prevent thereby any its displacement relative to this aorta 200. Then stapler 1 is brought into inoperative position necessary for its free removal and removed from graft 3 and from aorta 200.

At the second stage in the intravascular device—graft 3 there is made an incision 206 for access to its lumen (FIG. 13). Then, through previously created duct 202 and incision 206, there is inserted into the lumen of graft 3 second special stapler 1 for securing second end 208 of this graft 3 to the wall of aorta 200. This stapler 1 is brought into operative position whereupon its actuator with U-shaped staples 28 located in die 14 at its free end is brought to the wall of graft 3, at the point of securing its second end to the wall of aorta 200. There is checked the matching of mutual positioning of second end 208 of graft 3, the spot of its supposed securing to the wall of aorta 200, as well as of the actuator of second stapler 1 with U-shaped staples 28. When in the actuator of this second stapler 1 there is generated an axial force sufficient to act on U-shaped staples 28, the latter, extending from die 14 in radial direction, punch not only the wall of graft 3, but also the surrounding wall of aorta 200 in such a way that the distal ends of these U-shaped staples 28 extend in part outside aorta 200 and are bent over on its outer surface to form a rigid connection of the second end 208 of graft 3 with the wall of aorta 200. Then the actuator of second stapler 1 is moved clear of the wall of graft 3, whereby U-shaped staples 28 remain fixed in the wall of graft 3 and in the wall of aorta 200 to secure the second end 208 of graft 3 to a corresponding portion of aorta 200 and thereby prevent any its displacement relative to this aorta 200. Next, stapler 1 is brought into inoperative position necessary for its free removal from graft 3 and removed therefrom and from aorta 200.

At the last step incision 206 in graft 3 and duct 202 for access to the lumen of graft 3 and to the lumen of operated aorta 200 are closed via surgical procedure. Due to the above manipulations there is created a secure multiple-point connection of graft 3 with the wall of aorta 200 which prevents displacement of this graft 3 from an assigned position due to blood flow and peristelsic oscillations of the walls of aorta 200.

According to the suggested method, it is also possible to secure the ends of another intravascular device, such as stent-graft 220 (FIG. 14), having a broad proximal part 222 and bifurcated distal part 224 and 226 to the wall of aorta 200. This is accomplished via a set of at least two staplers 1 and using in each of them simultaneously at least two fastener means—U-shaped staples 28. The set contains at least one first stapler for securing broad proximal part 222 of stent-graft 220 to the wall of aorta 200 and at least one second stapler for securing to the wall of aorta 200 bifurcated distal part 224 and 226 of stent-graft 220. Securing the end of a stent-graft having a broad proximal part 222 to the wall of aorta 200 in the area of neck 228 of aorta 200 is performed via the first of staplers 1 comprised in the stapler set and using simultaneously at least two U-shaped staples 28.

The distal end of stent-graft 220 having a bifurcated distal part 224 and 226 is secured to the wall of aorta 200 via the second of staplers comprised in the set and using simultaneously at least two U-shaped staples 28. The securing is performed near the free end of one 224 or other 226 of the branches of bifurcated distal part of this stent-graft 220.

At last, according to the claimed method, stent-graft 220 may be secured to the wall of aorta 200 also using at least two U-shaped staples 28 near the free end of both branches 224 and 226 of bifurcated distal part of stent-graft 220.

Application of the suggested new and improved method of securing in combination with a new stapling device-laparoscopic stapler 1 operating on the base of this method allows, in the opinion of the authors, to solve the problem of providing secure and relatively simple means of securing intravascular devices 3 to blood vessel walls. In particular, their application will allow to solve the problem of securing stent-graft 220 to the wall of aorta 200 or securing to blood vessel walls grafts 3 or other similar devices if these devices have no sufficient fixation of their own for preventing their displacement from assigned positions.

While this invention has been described in conjunction with specific embodiment thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

The invention claimed is:

1. A stapler for laparoscopic aortic repair by intraluminal fixation of an intravascular device, including a graft or a stent-graft, to a blood vessel, comprising:

a tubular body configured for positioning within the blood vessel, said tubular body being rigid in longitudinal direction and flexible in lateral direction, the tubular body carrying, a substantially cylindrical head disposed at one end of the tubular body, the cylindrical head having an inner cavity, a proximal end and a distal end; the cylindrical head being connected to a die loadable with fastener means, including U-shaped staples, the die being configured as a barrel having a proximal end, a distal end, a substantially cylindrical peripheral surface and an inner cavity open at the distal end, said barrel having radial slots opening at the peripheral surface, and said die having recesses at the proximal end thereof provided with grooves for receiving the fastener means while each of said grooves being configured with a couple of curvilinear guiding faces located adjacent to the peripheral surface of the die and diverging towards the peripheral surface of the die such that free ends of said fastener means are bent when the fastener means are displaced along the grooves towards peripheral surface of the die; the die being closed by a die lid having a through axial hole, a substantially cylindrical peripheral surface, a proximal and distal end face, a plurality of radial slots extending onto said cylindrical surface, as well as a means for retaining the free ends of the fastener means in the grooves and means for separating the fastener means from the stapler at the end of a working stroke, said stapler further comprising, a control mechanism disposed at a second end of the tubular body opposite to said head, said mechanism comprising a cylindrical hollow body delimited by a proximal end and a distal end, said hollow body being connected to a retaining handle extending from the distal end sidewise at an angle from about 30 degrees to about 90 degrees, and said control mechanism further comprising, a control lever pivotally mounted on said retaining handle and a pressure rod located within said hollow body, having a longitudinal axis, a proximal end and a distal end, the pressure rod being rigid in longitudinal direction and flexible in lateral direction and being operatively associated via its distal end with said control lever and its proximal end being located in the inner axial cavity of said die to allow for reciprocating therealong, said control mechanism further comprising a plurality of pivotable levers, deployed within the axial cavity of the cylindrical head that pivot upon application of axial force by the pressure rod, pivoting of said pivotable levers resulting in application of a radial force to a fastener means causing its radial displacement along the grooves; said stapler further comprising means for temporary fixation on the stapler body of intravascular devices, when it is put over the stapler body, said means for temporary fixation comprising an adjusting screw to displace the pressure rod to such an extent that the free ends of the fastener means punch the wall of said intravascular device and prick the intravascular device.

2. A stapler according to claim 1, wherein said substantially cylindrical hollow body of the control mechanism has a proximal end and a distal end with retaining handle extending from this distal end sidewise at a certain angle, from about 30 degrees to about 90 degrees, this retaining handle being provided with a swing lock and control lever pivotally mounted on said retaining handle, said control lever having a pressure end movably mounted within the hollow body in the clearance between the spring-loaded end of said pressure rod and adjusting screw coaxial with this pressure rod.

3. A stapler according to claim 1, wherein said die for receiving fastener means is shaped as a barrel with a substantially cylindrical generatrix and inner axial cavity open on the side of the distal end of this barrel and terminating in a bottom at the proximal end of said barrel, the die has through, evenly disposed radial slots on its bottom, and on the end face of this bottom presented to said die bottom—recesses with grooves for receiving fastener means, substantially U-shaped staples, and with means for setting apart the ends of the fastener means, these recesses with grooves have substantially the same depth relative to said end face of the die bottom and are coaxial with the radial slots.

4. A stapler according to claim 1, wherein said die for receiving fastener means, substantially U-shaped staples, is shaped as a barrel with a substantially cylindrical generatrix and inner axial cavity open on the side of the distal end of this barrel and terminating in a bottom at the proximal end of said barrel, the die has through, evenly disposed radial slots on its bottom, and on the end face of this bottom presented to said die lid-recesses with grooves for receiving fastener means and with means for setting apart the ends of the fastener means, these recesses with grooves have substantially different depths relative to said end face of said die bottom and are coaxial with the radial slots.

5. A stapler according to claim 4, wherein said recesses with grooves have at least two different depths relative to said end face of the die bottom, recesses with grooves of different depths alternating with one another.

6. A stapler according to claim 1, wherein said fastener means are formed substantially as U-shaped staples and located radially in said grooves of said stapler die to extend radially from these grooves due to radial forces, the free ends of said U-shaped means being disposed on both sides of said means for setting apart the ends of these fastener means located along the axes of said grooves, immediately adjacent to the cylindrical generatrix of said die and being substantially V-shaped;

7. A stapler according to claim 6, wherein said means for setting apart the ends of said fastener means, substantially U-shaped staples, are disposed along the axes of grooves, immediately adjacent to the cylindrical generatrix of said die and are substantially V-shaped, with lateral guiding faces which are substantially curvilinear, concave and diverging from one another in direction from the center of said die towards its cylindrical generatrix, which allows to bend outward the free ends of fastener means during their extension from the die due to said radial forces.

8. A stapler according to claim 6, wherein said means for setting apart the ends of said fastener means, substantially U-shaped staples, are disposed along the axes of grooves, immediately adjacent to the cylindrical generatrix of said die and are substantially V-shaped, with lateral faces, which are substantially radial, concave and diverge from one another in direction from the center of said die towards its cylindrical generatrix, which allows to bend outward the free ends of fastener means during their extension from the die due to said radial forces.

9. A stapler according to claim 1, wherein said die lid is provided with means for retaining the free ends of said fastener means, substantially U-shaped staples, which contain torsion spring elements disposed near the points of intersection of said radial slots with said distal end face and said cylindrical generatrix of this die lid.

10. A stapler according to claim 1, wherein said die lid is provided with means for separating from this stapler the middles of said fastener means, substantially U-shaped staples, at the end of their working stroke, these means containing recesses located near the points of intersection of said radial slots with said distal end face and said cylindrical generatrix of this die lid.

11. A stapler according to claim 1, wherein said die lid is made of a transparent material for checking the state of fastener means, substantially U-shaped staples.

12. A stapler according to claim 1, wherein said pressure rod has a longitudinal axis, substantially conical proximal end, distal end and thrust collar near its distal end, this pressure rod is rigid in longitudinal direction and flexible in lateral direction, the pressure rod being spring-loaded, operatively associated by its distal end with said control lever and capable of reciprocation by its distal end—within said hollow body of the control mechanism, and by its substantially conical proximal end—within said inner axial cavity of the die.

13. A stapler according to claim 12, wherein said pressure rod has a substantially conical proximal end with a cone vertex angle from about 3 to about 35 degrees.

14. A stapler according to claim 13, wherein said pressure rod has a substantially conical proximal end with a cone vertex angle from about 10 degrees to about 20 degrees.

15. A stapler according to claim 1, wherein said means for transmitting axial force from said pressure rod to said fastener means, substantially U-shaped staples, and for transforming this axial force into radial forces applied to each of these U-shaped staples contain curved L-shaped levers pivotally mounted by the ends of their long arms near the free end of said hollow body and evenly arranged within said inner axial cavity of the die in such a way, that their short arms bent outward relative to the longitudinal axis of the die, are disposed in corresponding through radial slots on the bottom of this die, said curved L-shaped levers being configured to periodically cooperate by inner faces of their long arms with said substantially conical proximal end of the pressure rod, and by their free ends of short arms bent outward—with the middles of corresponding U-shaped staples.

16. A stapler according to claim 15, wherein said curved L-shaped levers are pivotally mounted by the ends of their long arms on a ring located within said inner axial cavity of the die, in a clearance between the free end of said head and inner ribs of this die extending from the wall of its inner axial cavity in direction to the die longitudinal axis, said ribs having evenly arranged radial slots, and in each of the latter there is movably located a corresponding curved L-shaped lever.

17. A stapler according to claim 1, wherein said die, die lid and fastener means, substantially U-shaped staples located in the die grooves form in combination a single set of the stapler actuator which is configured to be removed from said stapler body and then replaced by other, similar interchangeable sets.

18. A stapler according to claim 1, wherein said means for temporary fixation on the stapler body of delivered intravascular devices, substantially grafts or stent-grafts, located on this stapler body outside contains substantially an adjusting screw with a thrust head located in the distal part of said body of the control mechanism, coaxially with said pressure rod and on the other side of the pressure end of said control lever, as well as fastener means, substantially U-shaped staples, wherewith said adjusting screw is operatively associated via the pressure end of said control lever and said pressure rod.

* * * * *